United States Patent
Curcic et al.

(10) Patent No.: US 10,813,358 B2
(45) Date of Patent: Oct. 27, 2020

(54) COMPOSITE PARTICLES FOR CONTROLLING ARTHROPOD INFESTATION

(71) Applicant: Terramera Exco Holdings Ltd., Vancouver (CA)

(72) Inventors: Igor Curcic, Winchester (GB); Martin Brown, Petersfield (GB); David Grzywacz, Faversham (GB); Kenneth Wilson, Lancaster (GB)

(73) Assignee: Terramera Exco Holdings Ltd., Vancouver (CA)

( * ) Notice: Subject to any disclaimer, the term of this patent is extended or adjusted under 35 U.S.C. 154(b) by 0 days.

(21) Appl. No.: 15/743,707

(22) PCT Filed: Jul. 28, 2016

(86) PCT No.: PCT/EP2016/068097
§ 371 (c)(1),
(2) Date: Jan. 11, 2018

(87) PCT Pub. No.: WO2017/017234
PCT Pub. Date: Feb. 2, 2017

(65) Prior Publication Data
US 2018/0206503 A1 Jul. 26, 2018

(30) Foreign Application Priority Data

Jul. 29, 2015 (GB) .................. 1513398.6

(51) Int. Cl.
| | | |
|---|---|---|
| *A01N 63/00* | (2020.01) | |
| *A01N 25/04* | (2006.01) | |
| *A01N 25/10* | (2006.01) | |
| *A01N 25/26* | (2006.01) | |
| *C12N 1/20* | (2006.01) | |

(52) U.S. Cl.
CPC ............ *A01N 63/00* (2013.01); *A01N 25/04* (2013.01); *A01N 25/26* (2013.01); *C12N 1/20* (2013.01); *C12N 2710/14031* (2013.01)

(58) Field of Classification Search
None
See application file for complete search history.

(56) References Cited

U.S. PATENT DOCUMENTS

| | | | |
|---|---|---|---|
| 5,560,909 A | | 10/1996 | Rheaume et al. |
| 5,665,349 A | * | 9/1997 | Levings, III ........... A01N 63/00 424/93.2 |
| 5,965,123 A | | 10/1999 | Ahmed |
| 6,156,309 A | | 12/2000 | Miller et al. |
| 6,521,454 B1 | | 2/2003 | Becnel et al. |
| 2014/0086969 A1 | | 3/2014 | Shih et al. |

FOREIGN PATENT DOCUMENTS

| | | | |
|---|---|---|---|
| GB | 2 481 307 B | 10/2014 | |
| WO | 92/10170 A1 | 6/1992 | |
| WO | 96/01055 A1 | 1/1996 | |
| WO | WO-0226040 A1 * | 4/2002 | ............ A01N 63/00 |
| WO | 2008/062221 A2 | 5/2008 | |
| WO | 2011/148144 A1 | 12/2011 | |
| WO | 2014/020295 A1 | 2/2014 | |

OTHER PUBLICATIONS

Arghya et al. (PEGincorporated polymeric microcapsules for intramyocardial delivery of stem cells genetically modified by baculovirus, : An Interdisciplinary Integrative Forum on Nanotechnology, Biotechnology and Microtechnology, Boston, MA, United States, Jun. 13-16, 2011 (2011), vol. 3, 338-340 (Year: 2011).*
British Combined Search and Examination Report issued in GB 1513398.6 dated Jan. 28, 2016.
Written Opinion of the International Searching Authority of PCT/EP2016/068097 dated Sep. 5, 2016.
International Preliminary Report on Patentability of PCT/EP2016/068097 dated Oct. 16, 2017.
International Search Report of PCT/EP2016/068097 dated Sep. 5, 2016.

* cited by examiner

*Primary Examiner* — Alton N Pryor
(74) *Attorney, Agent, or Firm* — Oyen Wiggs Green & Mutala LLP

(57) ABSTRACT

Composite particles comprising baculovirus particles in a coating of wax that is degradable in the gut of a larva of an arthropod species, optionally in conjunction with an insecticide, methods of manufacture, uses thereof, and methods of controlling arthropod infestations.

21 Claims, No Drawings

COMPOSITE PARTICLES FOR CONTROLLING ARTHROPOD INFESTATION

CROSS REFERENCE TO RELATED APPLICATIONS

This application is a National Stage of International Application No. PCT/EP2016/068097 filed Jul. 28, 2016, claiming priority based on British Patent Application No. 1513398.6 filed Jul. 29, 2015, the contents of all of which are incorporated herein by reference in their entirety.

The present invention relates to compositions, particles and uses thereof, methods for controlling pests and methods of producing compositions and particles for the control of pests. In particular, the invention relates to compositions and particles comprising entomopathogenic viruses, their uses on plant material, methods for controlling pests with entomopathogenic viruses, and processes for producing particles and particles of use in controlling pests employing such organisms.

The human population of the world is increasing and is expected to plateau by 2030 at about 9 billion. As the population increases there is an ever expanding need to produce more food to feed it, and concomitantly, farmed animals such as livestock, fish, poultry and other animals on which the human population depends, at least in part. Much of the food source that is required for humans, livestock and other farmed animals is provided in the form of plants and plant-derived matter from cultivated cereals, vegetables, fruit bearing plants such as bushes, strawberries, raspberry canes, gooseberries, vines such as grape vines, passionfruit and kiwifruit and the like, and trees for nuts such as hazelnuts, almonds, walnuts, brazil nuts, cashew nuts and the like; oil generation from trees such as palm oil, nut oils and the like; and fruit production from trees such as citrus fruits, apples, pears, peaches, plums, mangoes, papayas, and the like. Other plant resources that are used and/or cultivated by mankind include woody plants such as trees for wood e.g. for use in building construction, boat building, furniture manufacture and fencing; plants cultivated for the production of clothing materials, such as cotton, hemp and linen and the like.

Plants of agronomic importance to man are constantly open to attack from pests such as arthropods which deposit eggs on aerial parts and underground parts of the plants. The eggs hatch into larvae which then feed on the plants leading to lower yields per unit area of farmed land and increased numbers of newly generated arthropods. If left unchecked, resultant economic losses are significant, and may become substantial or in major crop infestations may result in the loss of entire crops.

It is a constant battle to keep one step ahead of arthropod evolution and/or to maintain or improve arthropod controlling activities where the use of chemicals over time indicates that arthropod species are developing resistance.

One problem associated with the conventional use of chemical agents provided in liquid form against arthropods in the field is that while the chemical agents provided may be effective for short periods of time after application, over longer periods of time, the level of activity tends to drop off and/or target pests develop resistance. As a result, the user has to apply chemicals more frequently in order to maintain control over arthropod infestation. This in turn means that the environs to which the chemicals are applied will receive high chemical loads often and this may have an adverse effect on the environment, and in particular on animals such as mammals, including humans, as well as other kinds such as birds, amphibians, and beneficial arthropods such as bees, aphid-eating ladybirds, spiders and butterflies.

Biological agents have been used in the past and are used today to control insect pests.

Certain biological agents that have proven useful in the control of arthropods on crops include the invertebrate-specific baculoviruses. The baculoviruses are circular DNA viruses that can be divided into four genera: Alphabaculovirus (lepidopteran-specific nucleopolyhedroviruses [NPVs]), Betabaculovirus (lepidopteran-specific Granuloviruses [GVs]), Gammabaculovirus (hymenopteran-specific nucleopolyhedroviruses) and Deltabaculovirus (dipteran-specific nucleopolyhedroviruses). Of these genera, the most important ones for the purpose of the present invention are the two genera: nucleopolyhedroviruses (NPVs) and granuloviruses (GVs).

GVs contain only one nucleocapsid per envelope, and NPVs contain either single (SNPV) or multiple (MNPV) nucleocapsids per envelope. The enveloped virions are further occluded in a granulin matrix (GVs) or in a polyhedrin matrix (NPVs). Furthermore, GVs have only a single virion per granulin occlusion body while polyhedra can contain multiple embedded virions.

The baculoviruses tend to have a narrow host arthropod range, that is to say, insect range, and infectivity is restricted to the original host genus or family. Baculoviruses have the additional advantage of being substantially non-toxic to vertebrates such as mammals, including humans, and are generally not known to be toxic to beneficial insects, birds or to aquatic organisms.

Compositions comprising baculovirus for use in controlling insect pests are known in the art. U.S. Pat. No. 6,521,454 provides an insecticidal composition comprising (a) a baculovirus effective for producing a lethal or debilitating infection in an insect and (b) at least 1 mM of a divalent cation.

However, one of the problems with baculoviruses, and for the purposes of the present invention the NPVs and GVs in particular, is that they are susceptible to UV degradation, typically showing a field persistence on crops of 2-7 days post application when applied in conventional commercial formulations. This problem was partially addressed in US 2014/086969 which discloses UV-resistant gelatin/silica coated viral particles and methods for controlling agricultural insect pests using the same.

Baculoviruses are also known to be temperature sensitive. Certain baculoviruses, such as the NPV of Mulberry have been shown to be vulnerable to temperatures of 50° C., at which temperature they are inactivated and can no longer infect and kill target arthropods (Priyadharshini & Narayanaswamy (2012) EJBS 5(1) pp 22-26. Other baculoviruses have been shown to be vulnerable to temperatures of 60° C. or higher, such as the Codling moth virus (Pemsel M. et al (2010) The Journal of Supercritical Fluids, 53, 174-178). The susceptibility of viruses of use in the invention to heat has resulted in the creation of virus encapsulation methods in the prior art that result in particles that employ gas saturated solutions in which the temperature has been kept low, that is to say below 60° C. (Pemsel et al ibid). WO 96/01055 describes a general encapsulation method and product thereof for use in preparing food products. In more detail, a food product is disclosed comprising a matrix of fibres having inclusion bodies dispersed therein.

A further problem associated with conventional commercial formulations is that the virus of choice is typically suspended in naked form in an aqueous formulation which contributes to limiting or reducing the shelf-life of the virus through the action of oxidative processes.

There exists a need to provide more UV-stable formulations of viral agent of choice for use on crop plants. There exists a further need to provide formulations in which the virus of choice is less susceptible to oxidation.

A further need is to provide improved formulations containing viral agents of choice for use in the field, that is to say on growing crops and/or on harvested or 'cut' produce, and in the storage of food including processed dried comestibles, grains, and processed products derived therefrom.

A perceived advantage of the present invention is to provide pesticide formulations that persist longer in the field and/or in storage than currently known formulations comprising baculoviruses.

A further perceived advantage of the present invention is to provide improved pesticide formulations comprising baculoviruses of choice that enable the control of pest larvae on plants which secrete plant chemicals on their aerial structures as a defence against plant viruses, such as legumes e.g. chick peas. Such plant secretions can reduce the effectiveness of a biological agent of choice if it is applied using conventional formulations (Stevenson, D'Cunha & Grzywacz, J Chem Ecol. 2010 February; 36(2):227-35. doi: 10.1007/s10886-010-9748-8. Epub 2010 Feb. 10).

These and other needs and advantages will become apparent from the following description and examples.

As a first aspect of the invention there is provided a composite particle comprising:

i) at least one baculovirus particle; and ii) an enveloping coating of wax for the baculovirus particle of i) made up of at least one wax that is degradable and/or soluble in the gut of a larva of an arthropod species; and iii) optionally, an insecticide that is ingestible by an insect larva, such as a pyrethroid and/or an organophosphate.

Naturally, the skilled addressee will understand that for the purposes of the present invention 'composite particle' refers to an individual particle. Such individual particles may be brought together forming a population of particles for use in application to crops and/or food produce. Such populations of particles may be in liquid or dry powder form depending on end purpose as outlined herein.

The virus particle may be selected from baculovirus particles of species of interest, such as from alphabaculoviruses and/or betabaculoviruses, namely, nucleopolyhedrosis viruses (NPVs) and/or granulosis viruses (GVs). Preferably, the baculovirus particle is in the form of an NPV or a GV baculovirus occlusion body. Suitable virus particles of use in the invention include baculovirus occlusion particles of NPVs or GVs, such as those selected from *Heliothis zea* NPV, *Helicoverpa armigera* NPV, *Spodoptera exigua* NPV, *Spodoptera littoralis* NPV, *Spodoptera exempta* NPV, *Anticarsia gemmatalis* NPV, *Lymantria dispar* MNPV, *Neodiprion abietis* NPV, *Orygia pseudotsugata* NPV, *Neodiprion lecontei* NPV, *Trichoplusia ni* NPV, *Autographa californica* NPV, *Spodoptera albula* NPV, *Spodoptera litura* NPV, *Cydia pomonella* GV, *Plutella xylostella* GV, *Cryptophlebia leucotreta* GV, *Phthorimaea operculella* GV, *Adoxphyes orana* GV, *Homona maganima* GV, *Plodia interpunctella* GV, *Adoxophyes honmai* GV and the like. Preferably, the viral biological agent is selected from *Heliothis zea* NPV, *Helicoverpa armigera* NPV, *Spodoptera exigua* NPV, *Spodoptera littoralis* NPV, *Spodoptera exempta* NPV, *Anticarsia gemmatalis* NPV, *Cydia pomonella* GV and *Plodia interpunctella* GV depending on purpose and proposed application in the field. Occlusion bodies of NPV baculoviruses are of the order of 0.15 µm to 15 µm in length and those of GV baculoviruses are of the order of 170-500 nm in size, depending on species. The virions of NPV species are of the order of 230-420 nm in length while those of GV species are of the order of 260 nm-500 nm in length.

The virus particle is at least partially enveloped or encapsulated in wax. It is thought that the degree of envelopment or encapsulation of individual virus particles of use in the invention by a suitable wax-containing material should be a minimum of at least 30%, preferably at least 50% and preferably still at least about 80%, 90% or 95%. Most preferably, the virus particle of choice of use in the invention is fully enveloped in a wax or a blend of waxes that is capable of being broken down or degraded and/or solubilised in the gut of a target pest larva and/or larvae. For the purposes of the present invention the words 'larva' and 'larvae' used herein refer to insect larvae of species that prey on domestic crops, plants of commercial benefit to mankind and plant products whether processed or otherwise that are derived from plants such as wood, dry comestibles, and clothing materials including those referred to herein. The words 'larva' and 'larvae' are used interchangeably unless context demands otherwise. The envelopment by wax shields the virus particle of choice from exposure to UV and other environmental hazards, such as oxidising conditions. Suitable waxes include those that solubilise or degrade or surface etch enough to release at least one viable virus particle in a larval gut environment, for example, in a basic pH. Such waxes are typically selected from natural waxes that are ingestible by larvae, such as carnauba wax, rice bran wax, candelilla wax, sugar cane wax, ouricouri wax, synthetic waxes, such as amide waxes, polyethylene waxes, functionalised polyethylene waxes, oxidised polyethylene waxes and the like that are ingestible by the larva or a mixture or blend of two or more thereof. If a blend of two waxes is used the waxes may be employed in a ratio of 1:99 to 99:1, preferably a ratio of 5:95 to 95:5, or any suitable ratio thereinbetween, such as a 50:50 blend of natural waxes, for example of rice bran wax and candelilla wax. In certain circumstances, ingestible waxes may be made up of a hard wax, for example, carnauba wax or montan wax and at least one softer wax that is ingestible by larvae of species of interest such as a natural or synthetic wax as described herein for example, candelilla wax, rice bran wax or a blend thereof may be further blended together. The purpose of adding a hard wax to softer waxes in blends of waxes of use in the invention is to optimise milling procedures. The waxes may also include an added feed stimulant such as sugars, for example, sucrose, fructose, palm sugar, golden cane syrup and the like admixed therein in particulate or liquid form, molasses, honey, sorbitol or other artificial or organic baits (Ballard J et al., Biocontrol Science and Technology, volume 10, Issue 5 pp 627-640 2000 DOI: 10.1080/095831500750016424), including volatiles selected from alcohols, esters and aromatic compounds, such as ethyl acetate, 3-methylbutanol, ethyl hexanoate, 2-phenylethanol, ethyl octanoate, ethyl (E)-4-decenoate, ethyl decanoate, ethyl dodecanoate and the like (EI-Sayed A. M., *J. Agric. Food Chem.*, 2005, 53 (4), pp 953-958 DOI: 10.1021/jf048521j), or other plant extracts or a larvae attractant, such as a larvae aggregation pheromone, for example that of *Cydia pomonella* (Jumean et al. (2004), The Canadian Entomologist, vol. 136, pp. 871-873). Further additives that may be added to or included in composite particles of the invention include Neem oil, and/or azidirachtin which may synergise with the virus (Nathan and Kalaivani, (2005), Biological Control, 34(1) pp.93-98).

In addition, a wax that may be used in the present invention can be made up of several different waxes melted to form a liquid or melded together under pressure or heat using a temperature sufficient to soften the wax(es) such that baculovirus particles of choice may be added and at least partially encapsulated therein. Once the baculoviral agent of choice is added to the wax, the wax may be cooled to solidity quickly and then kibbled, comminuted and/or air jet milled to a desired particle size using conventional equipment and procedures known in the art.

Such additional waxes may be selected from mineral waxes and synthetic waxes provided that at least one wax, preferably a natural wax or a blend of natural waxes as described herein, that is degradable and/or digestible in the larval gut (e.g. through enzyme digestion and/or being soluble in a larval gut environment of pH 8 to 12 in the gut of a larva of interest) is in the melt or mixture and the baculoviral agent is able to be released from wax blends in the gut of the larva. Typically, natural waxes of use in the invention have a melting temperature of ≥40° C., depending on design. Suitable natural waxes of use in the invention include waxes having a melting point of preferably ≥50° C., and most preferably are made up of hard waxes having a melting point of ≥70° C. Examples of natural waxes of use in the present invention include carnauba wax, beeswax, Chinese wax, shellac wax, spermaceti wax, myricyl palmitate, cetyl palmitate, candelilla wax, castor wax, ouricury wax, wool wax, sugar cane wax, retamo wax, rice bran wax and the like.

Synthetic waxes that may be melted together with or melded under pressure with natural waxes soluble in the gut of a target larva include waxes selected from paraffin wax, microcrystalline wax, polyethylene waxes, Fischer-Tropsch waxes, substituted amide waxes, polymerized α-olefins and the like, provided always that the target larva is capable of ingesting such synthetic waxes. Further waxes that may be melted together with or melded under pressure with natural waxes degradable in the gut of a target larva include mineral waxes selected from montan wax (e.g. Lumax® Bayer) ceresin wax, ozocerite, peat wax and the like, provided always that the target larva is capable of ingesting such mineral and/or synthetic waxes and that the partially encapsulated or wholly encapsulated virus particles of choice are releasable therefrom.

An optional component in the form of a pyrethroid or an organophosphate insecticide may be added to composite particles of the invention to improve the efficacy of virus control of insect species of interest, such as Lepidopteran species of interest. Suitable insecticides that may be added to composite particles of the invention containing baculovirus particles of interest include α-cypermethrin, λ-cyhalothrin, [cyano-(3-phenoxyphenyl)-methyl]-3-(2,2-dibromoethenyl)-2,2dimethylcyclopropane-1-carboxylate (deltamethrin), i-fluvalinate, pirimiphos methyl, chlorpyriphos, malathion, terbufos, phosmet, tiamethoxam, clothiandin, acetamiprid, spinosad, rynaxapyr and the like.

Arthropod species which may be targeted by composite particles of the invention include crop pest species of the *Lepidoptera*, pest species of the *Diptera*, and pest species of the *Coleoptera* such as of the *Scarabaeidae*. The insect pests that may be targeted using composite particles of the invention are typically members of the Lepidoptera and include the larvae of *Lepidoptera* species that infest food processing and food storage sites, such as Tobacco moth also known as Warehouse moth (*Ephestia elutella*), Mediterranean Flour moth (*Ephestia Kuehniella*) [also known as 'Indian Flour moth' and 'Mill moth'], Raisin moth (*Cadra figulilella*), Almond Moth (*Cadra cautella*) and Indian Meal moth (*Plodia interpunctella*). Other insect pests that infest growing crops which may be targeted using composite particles of the invention include the larvae of Corn earworm also known as the tomato fruitworm or Tobacco budworm [*Helicoverpa zea*], Cotton bollworm, Podborer [*Helicoverpa armigera*], Beet armyworm [*Spodoptera exigua*], Egyptian cotton leafworm [*Spodoptera littoralis*], African armyworm *Spodoptera exempta*, Velvetbean caterpillar [*Anticarsia gemmatalis*], Gypsy moth [*Lymantria dispar*], Codling moth [*Cydia pomonella*], Diamond back moth [*Plutella xylostella*], False Codling moth [*Thaumatotibia ieucotreta*], Potato tuber moth [*Phthorimaea operculella*], Summer fruit tortrix moth [*Adoxphyes orana*], Oriental tea tortrix moth [*Homona magnanima*], and Smaller tea tortrix moth, [*Adoxophyes honmai*].

In a further aspect of the invention there is provided a method of producing composite particles of the invention by:

i) melting at least one wax;

ii) adding baculovirus particles to the molten wax of i) and admixing therewith for a time period sufficient to at least partially coat the virus particles;

iii) rapidly cooling the product of ii) to a solid; and iv) kibbling and comminuting the product of iii) to a particle size for ingestion by a larva.

In step i), the wax may be a single wax or a mixture of waxes as described herein. The wax of i) may be melted forming a liquid phase to which virus particles of choice, for example baculovirus particles such as occlusion bodies, are then added and admixed therewith in step ii) to form a homogeneous mixture using a high energy mixer, before rapidly cooling down the product of ii) to a solid form. The cooling step iii) is rapidly achieved, for example, by pouring the liquid admixture of ii) into a large shallow tray or other suitable receptacle that is then placed inside a suitable freezing means, such as a freezer, and held at a temperature in the range of about minus 5° C. to minus 30° C., such as at minus 24° C. Further means to attain rapid melting in i) and cooling of the product of ii) in step iii) includes the use of commercially available mantle vessels, such as the Style D kettle with super jacket available from Lee Industries, Philipsburg, USA, that are capable of heating admixtures of the invention to high liquefying temperatures and then rapidly cooling them to an intermediate temperature, such as the melting temperature of the blend, prior to pouring the cooled liquid into a receptacle such as a tray and refrigerating further, forming a solid body of wax. It has surprisingly been found that baculovirus particles, such as baculovirus occlusion bodies, are able to withstand high extremes of temperature for short periods of time without significant loss of viability. Baculovirus particles have been shown by the inventors to withstand and survive heating temperatures of up to 140° C. for short periods of time, for example for up to 5 minutes without significant detriment to viability. Furthermore, the inventors have found that viruses are able to withstand and survive low temperatures, for example low temperatures down to about minus 25° C. for short periods of time of up to 12 hours or so, preferably of periods of time of 1 to 5 hours, for example, 1 to 2 hours, and remain viable thereafter. It is the unexpected finding that baculovirus particles are surprisingly resilient to temperature extremes that make the present invention possible since prior to making the invention it was thought that baculoviruses were not capable of withstanding temperatures above 50° C. and so using a liquid wax-based formulation to encapsulate baculoviruses was not considered feasible.

Once the cooling step of iii) is completed, the resultant block of wax may then be kibbled, comminuted and micronized to particle sizes of a desired volume mean diameter such as in the range from 1 µm to 200 µm, preferably from 1 µm to 100 µm, more preferably from 1 µm to 50 µm, still more preferably from 2 µm to 40 µm, for example, from 5 to 30 µm, 8 to 15 µm and most preferably from 10 to 15 µm as outlined herein.

Particle size is suitably measured using methods and apparatus recognized as standard in the art. Particle sizing in dispersions can be accomplished using a variety of techniques, including laser diffraction, dynamic light scattering (DLS), disc centrifugation, and light microscopy. All of these techniques have their advantages and limitations. Laser diffraction relies on a well-controlled presentation of the sample to the measurement region and is limited to samples with narrow range of particle concentrations. Dilution is often required and this may affect the particle size, particularly in compounds with high solubility. Examples of sizing equipment are made by Malvern Instruments (UK), using laser diffraction methods. For highly irregular particles, the diameter refers to the greatest diameter in any dimension even if the particle is relatively non-spherical.

The skilled addressee will appreciate that where composite particles of the invention are produced according to this aspect of the invention a chemical pesticide may be added to the molten wax of step i), above. Suitable chemical pesticides include those selected from organophosphates and pyrethroids such as α-cypermethrin, λ-cyhalothrin, [cyano-(3-phenoxyphenyl)-methyl]-3-(2,2-dibromoethenyl)-2,2-dimethyl-cyclopropane-1-carboxylate (deltamethrin), τ-fluvalinate, pirimiphos methyl, chlorpyriphos, malathion, terbufos, phosmet, tiamethoxam, clothiandin, acetamiprid, spinosad, rynaxapyr and the like.

In a further aspect of the invention there is provided use of composite particles as defined herein in the control of larval infestation on crop plants in the field preferably in the reduction of viable numbers of larvae on crop plants. Use on crop plants in the field includes use on fruit trees, such as apple, pear, cherry and peach trees, crucifer vegetables such as cabbage, broccoli, brussels sprouts and kale, cereals such as corn (maize), wheat, rye, barley and sorghum, rice, nut trees such as almond, pecan, hazelnut, brazil, and cashew, grape vines, evergreen trees such as Douglas fir, Loblolly pine, cotton, beans such as velvet bean, solanaceous species such as potato, tomato, eggplant, capsicum, tobacco and petunia.

Composite particles of the invention may be used prophylactically on or in harvested and/or processed crop produce to minimise the risk of infestation by Lepidopteran pests. Harvested and/or processed crop produce in dried form may be located in storage areas such as grain storage areas, including grain silos and grain bins where grain is stored immediately after harvest or prior to processing. Other dried food and grain storage areas include warehouses where dried food and grain is stored prior to shipment, and transport facilities such as those of shipping containers, the holds of ships, trucks and the like. Use on harvested and/or processed crop produce includes use on dried commodities including whole grains such as wheat, rice, barley and corn (maize), pulses, beans, and lentils and products derived from or made with dried commodities such as processed foods including pasta, grain flours, couscous, breakfast cereals, dried herbs, domestic livestock feed, for example for pigs, cows, sheep and horses, semolina, breads, nuts (ground, flaked and/or whole nuts), snacking food, such as sweet and savoury items including biscuits, potato crisps, vegetable crisps, pretzels, cheese biscuits, and dried wafers.

In a further aspect of the invention there is provided a composition for application to crop plants that comprises composite particles as described herein. Such compositions may be comprised of particles in a liquid medium, that is to say, in the form of a suspension. Thus, as one alternative, there is provided a liquid formulation for controlling arthropod infestation of plants that comprises composite particles, wherein the liquid formulation is made up of:

i) particles of wax suspended within the liquid formulation that are degradable and/or soluble in the gut of larvae of at least one target arthropod species; and ii) at least partially encapsulated within the wax particles of i) at least one species of baculovirus in the form of baculovirus particles that has activity against the larvae of the target arthropod species of i); and iii) optionally, an insecticide selected from a pyrethroid and/or an organophosphate as defined herein. The liquid formulation of the invention typically has a volume mean diameter in the range from 1 µm to 200 µm, preferably from 1 µm to 100 µm, more preferably from 1 µm to 50 µm, still more preferably from 2 µm to 40 µm, for example, from 5 to 30 µm, 8 to 15 µm and most preferably from 10 to 15 µm as outlined herein.

The virus particles of use in liquid formulations of the invention are at least partially enveloped or encapsulated in waxes of choice as outlined herein. It is thought that the degree of envelopment or encapsulation of individual virus particles by a suitable wax-containing material of use in liquid formulations of the invention should be a minimum of at least 30%, preferably at least 50% and preferably still at least about 80%, 90% or 95%. Most preferably, the virus particle of choice of use in the invention is fully enveloped in a wax or a blend of waxes that is capable of being broken down or degraded and/or solubilised in the gut of a target pest larva and/or larvae.

The particles of the invention may be applied using either an aqueous liquid or an oleaginous liquid. In either format, the skilled addressee will appreciate that liquid compositions of the invention comprise composite particles that at least partially encapsulate and protect the virus particles from environmental elements such as UV light and oxidation. Preferably, the virus particles are fully encapsulated by the wax or wax admixture of the composite particles.

The liquid formulation of the invention may be formulated as an aqueous formulation or as an oleaginous formulation, depending on design. Aqueous formulations may include surfactants selected from commercially available ranges of surfactants sold under the trade marks such as Libsorb, Silwet, Tween, Span, Tensiofix, Brij, Torpedo, Newmans, Lansurf, Atplus, Atlox, Synperonic, Fortune, Guard, Rhino, Biopower, and the like. Of these surfactants, Tensiofix, and Span are most preferred.

Liquid formulations of this aspect of the invention may include additional feeding stimulants in liquid or solid form, as described hereinabove.

The liquid formulations according to this aspect of the invention may be applied to eukaryotic tissue selected from plant tissue, such as leaves, stems, fruiting bodies, and flowers.

Oleaginous formulations, that is to say oil dispersion (OD) formulations, may contain any oil suitable for use in the invention which may be selected from petroleum oils, such as paraffin oil, summer spray oils, the Solvesso® range of solvents, petroleum spirits and winter spray oils known in the art, and vegetable oils such as rapeseed oil, soybean oil, sunflower oil, palm oil and the like.

Composite particles of the invention once delivered to target surfaces are capable of adhering thereto, as the aqueous element of the composition evaporates or, in the case of an oleaginous element, the oil disperses and are available for ingestion by the feeding target larvae. The degree of encapsulation or envelopment of the biological agent of choice should be such as to protect the biological agent from environmental elements as alluded to herein. Target eukaryotic cell surfaces include plant surfaces of living plant tissue such as growing plants and harvested or 'cut' material, for example, leaves, stems, and flowers where target insect larvae may be found.

The composite particles of the invention as applied in liquid compositions should be effective in controlling populations of plant infesting target insect larvae through ingestion by the target larvae. The baculovirus particles of use in the invention must be capable of being released from composite particles of the invention inside the target larvae gut, and once released, be capable of killing the larvae.

The liquid compositions of the invention may include more than one baculovirus particle, for example a target larvae specific baculovirus as hereinbefore described and a further baculovirus particle, both of which have the capacity of controlling the infesting population of target pest larvae. Thus, compositions of the invention comprising composite particles of the invention carrying two different baculovirus particles of choice may be more efficient at killing target larvae. Thus, a single liquid composition of the invention may comprise composite particles of the invention that are loaded with at least two different baculovirus particles of the same or different species of choice that are capable of targeting the target pest larvae. Or, in an alternative, liquid compositions of the invention may include two or more composite particles wherein each composite particle is further loaded with different chemical pesticides selected from an organophosphate and a pyrethroid which are capable of targeting pest larvae. The chemical pesticide, if present, is typically added while the wax is in the molten state along with the baculovirus particle.

In a further aspect of the invention there is provided a dry powder composition that is effective in controlling arthropod infestation in storage products that comprises composite particles, wherein the dry powder composition is made up of:

i) particles of wax that are degradable and/or soluble in the gut of larvae of at least one target arthropod species; and ii) at least partially encapsulated within the wax particles of i) at least one species of baculovirus in the form of baculovirus particles that has activity against the said arthropod larvae; and iii) optionally, an insecticide selected from a pyrethroid and/or an organophosphate as defined herein.

The particles of wax in the dry powder composition of the invention typically have a volume mean diameter in the range from 1 μm to 200 μm, preferably from 1 μm to 100 μm, more preferably from 1 μm to 50 μm, still more preferably from 2 μm to 40 μm, for example, from 5 to 30 μm, 8 to 15 μm and most preferably from 10 to 15 μm as outlined herein.

The virus particles of use in dry powder compositions of the invention are at least partially enveloped or encapsulated in waxes of choice as outlined herein. It is thought that the degree of envelopment or encapsulation of individual virus particles by a suitable wax-containing material of use in dry powder compositions of the invention should be a minimum of at least 30%, preferably at least 50% and preferably still at least about 80%, 90% or 95%. Most preferably, the virus particle of choice of use in dry powder compositions of the invention is fully enveloped in a wax or a blend of waxes that is capable of being broken down or degraded and/or solubilised in the gut of a target pest larva and/or larvae.

The skilled addressee will appreciate that composite particles of the invention whether applied as dry powders or as liquid formulations may contain other desirable components such as additives selected from UV blockers such as oxyl methoyxcinnimate, modified soya oil, zinc oxide nanoparticles, beta-carotene or p-amino benzoic acid, colouring agents such as optical brighteners and commercially available colouring agents such as food colouring agents, plasticisers such as glycerine or soy oil, antioxidants such as vitamin E, butylated hydroxyl anisole (BHA), butylated hydroxytoluene (BHT), and other antioxidants that may be present, or mixtures thereof. The skilled artisan will appreciate that the selection of such commonly included additives will be made depending on end purpose. The skilled addressee will further appreciate that any additives to the composite particles of the invention should be ones that do not significantly interfere with the ability of the target larvae to ingest the particles.

In an alternative, composite particles of the invention may be presented to crop plants or harvested and/or processed crop produce as a dry powder.

In a further aspect of the invention, there is provided a method of controlling arthropod infestation, preferably in reducing arthropod infestation on grain or on processed comestibles wherein dry composite particles according to the invention are presented to the surfaces of grain or processed comestibles by i) collecting the composite particles in a dusting apparatus;

ii) releasing the said particles from the said dusting apparatus and onto the surfaces of said grain or processed comestibles.

In a further aspect of the invention, there is provided a method of controlling arthropod infestation, preferably in reducing arthropod infestation on grain or on processed comestibles wherein dry composite particles according to the invention are admixed with grain or processed comestibles.

In a still further aspect of the invention, there is provided a method of controlling arthropod infestation, preferably in reducing arthropod infestation in a storage area selected from a grain storage area and a dried food storage area wherein dry composite particles according to the invention are presented to the surfaces of the storage area by i) collecting the composite particles in a dusting apparatus;

ii) releasing the particles of i) from the dusting apparatus and onto the surfaces of the storage area.

In a further aspect of the invention there is provided a crop plant or cut harvested produce coated with particles as defined herein.

There now follow examples that illustrate the invention. It is to be understood that the examples are not to be construed as limiting the invention in any way.

EXAMPLES SECTION

Introduction

This work describes the method required to formulate virus in wax particle formulations.

Key:
BV: Baculovirus Occlusion Bodies raw material
NPV: Nucleopolyhedrovirus, a genera of the baculoviridae family of viruses included under the BV umbrella
GV: Granulovirus, a genera of the baculoviridae family of viruses included under the BV umbrella
EBV: Baculovirus occlusion bodies formulated into Entostat® particles through the methods described below
EBV+: Baculovirus occlusion bodies formulated into Entostat® particles through the methods described below, which also contain other additives of the types described previously in this document such as phagostimulants and aggregation pheromones.

1. Materials:
    Active ingredient (BV of the chosen species—SpliNPV targeting *Spodoptera littoralis*, or the Egyptian cotton leaf worm) sourced from NRI Candelilla wax and Rice bran wax.
2. Equipment:
    Hotplate that heats up to 150° C. (Stuart scientific Ltd)
    Two decimal place balance (Ohaus®)
    Freezer that cools down to at least −24° C. (any make/model will do)
    High shear mixer/homogenizer (IKA® T18 digital)
    Kibbler mill (KT handling limited model 04)
    Comminuting mill (Apex® LTD type 314s)
    Air jet mill (any make/model will do)
    Suitable size sample pots
3. Detailed Procedure
3.1. Using a calibrated balance weigh out the required quantity of carrier waxes—125.0 g of rice bran wax and 125.0 g of candelilla wax.
    Place a 50:50 mixture candelilla wax: rice bran wax (% w/w) into a pan and place onto a hotplate set to a temperature of 120° C. The wax is heated until completely melted and a clear liquid with no solids is observed.
    Using a calibrated balance a quantity of the active BV at 1% w/w is weighed out.
3.1.1. The BV is added to the molten wax quickly over a total time period of 60 s and dispersed within the molten wax by high shear mixing (using a high shear mixer IKA® T18) to ensure even distribution within the wax.
3.2. The wax is then transferred to a foil lined shallow tray and transferred to a freezer set at −24° C. to rapidly cool and solidify within approximately 1-2 h.
3.3. Once the formulated material is frozen into a completely solid block or slab it is broken into large chunks and sent for milling. The chunks are ground in a kibbler mill (KT Handling Limited, Model 04) to particles of approximately 2 mm average diameter
3.4. The kibbled material is then comminuted into smaller particles in a comminuting mill (model 314s, from Apex® Ltd) to particles of 150 μm average diameter.
3.5. The comminuted material is further micronized in a jet mill (Hosokawa® Alpine Jet AFG 100 fluidised bed jet mill) to achieve granulation of mean average particle size ~10 um.
3.6. The micronized material containing baculovirus particles (EBV) is stored in a suitable sample container under refrigeration conditions at 4° C., until use.
    Bioassay Methods
    The efficacy of the different EBV formulations is tested using two methods—the droplet method, using young neonate larvae, and the diet-plug method, using older (L3) larvae. All experiments will use larvae of the Egyptian cotton leafworm (*Spodoptera littoralis*).

Droplet method: EBV formulations are added to 10% sucrose solution containing food dye and a wetting agent (e.g. 1% Lankem AEP 66). A dilution series provides six EBV concentrations to provide reliable comparisons of LC50 values across different formulations (i.e. the concentration of EBV required to achieve 50% mortality). As positive and negative controls, the EBV concentrations are compared against the LC50 dose of the non-formulated SpliNPV virus, and the solution without any virus (i.e. sucrose solution, dye and wetting agent alone). For the bioassay, starved neonate larvae are placed in the centre of a Petri dish containing concentric circles of droplets of EBV solution. After 30 min feeding, larvae with blue guts (indicating that they have ingested the solution) are removed and placed singly into diet pots in an incubator at 27° C. Twice-daily monitoring of the larvae provides data on timing of death (or pupation) and its cause—larvae dying of viral infection are easily diagnosed visually, but is confirmed by microscopy. Bioassays use 50 larvae per treatment at each virus concentration, and the LC50 values of each EBV are calculated from five replicate assays using logistic regression.

Diet plug method: Starved 3rd-instar larvae are presented individually with a small cube (2 mm$^3$) of semi-artificial diet laced with 2 ml of the requisite EBV solution (or control solution) and left in an incubator overnight and next morning, larvae that have not eaten all of the diet plug are discarded. The remainder of the larvae are moved into individual diet pots and again monitored twice-daily for mortality/pupation. Sample sizes and analytical methods are the same as for the droplet bioassay.

Testing Effects of UV on EBV and EBV+ Formulations

Trial EBV and EBV+ formulations are tested initially in a sunlight simulator to quantify the effects of UV on the viability of the different EBV formulations compared to non-formulated virus and current commercial formulations (e.g. Littovir™). The EBV is exposed as dried suspensions of virus on mylothene laminated sheets—a system that has been developed at University of Greenwich to mimic plant leaf exposures. They are then exposed for 24 h to a Nereus CPS laboratory sunlight simulator which produces a UV spectrum comparable to sunlight. The test samples are cooled underneath by circulating temperature-controlled water. Exposed virus is then washed using a standard recovery protocol (sonication for 3 min then by wash for 1 h in 0.2% sodium dodecyl sulphate) to extract the exposed virus for neonate bioassay at LU. Promising candidate EBV+ are identified, longer-term (0-30 day) evaluations are carried out in UV weathering equipment, simulating both tropical and temperate cropping conditions with respect to UV, temperature and humidity levels. All treatments are applied using a droplet sprayer to mimic field application. The UV stability of the most promising EBV+ is compared to both non-formulated virus and commercially-formulated viruses. Targets are exposed to sunlight day-night cycles, and EBV+ samples are harvested at 0, 1, 2, 4, 8, 16 & 32 days for virus recovery. Exposed EBV+ is then neonate bioassayed at LU to determine biological activity and EBV+ half-life. Physical characteristics of exposed EBV+ are also determined by SEM.

Quantifying Persistence of EBV and EBV+ Formulations on the Crop

The persistence of the candidate EBV and EBV+ formulations is determined on two representative crop species: tomato and cabbage, grown in a glasshouse. Mature plants (30 per treatment) are sprayed with one of 2 rates of EBV+ solution (based upon commercial field application rates, validated via pilot studies), or with the EBV⁺ carrier alone (i.e. water+wetting agent; negative control) or the non-formulated SpliNPV virus solution (+wetting agent; positive control) or a commercial SpliNPV biopesticide (e.g. Littovir™) Immediately post-spraying, and then after 1, 2, 5, 10 or 20 days, a subset of plants is harvested for bioassays. Small disks (1 cm diameter) of leaf from sprayed plants are fed to starved third-instar larvae overnight in an incubator (27° C.). Larvae that have eaten all of the leaf the next morning are then transferred to a diet pot and their mortality/pupation monitored twice daily (30 larvae per sampling point per treatment group). In addition, and building on initial assessments made during EBV⁺ selection, at each sampling point the condition of the host plants used in the different treatments is compared to establish whether there are any short- or long-term negative effects of the UV blockers. Traits to be quantified include plant height, plant dry mass (above- and below-ground), leaf area and leaf colour.

The persistence of baculovirus particles of the invention is shown to be superior when compared to that of conventional formulations containing baculovirus.

The invention claimed is:

1. A composite particle comprising:
   i) at least one baculovirus particle; and
   ii) an enveloping coating of wax for the baculovirus particle of i) made up of at least one wax that is degradable and/or soluble in the gut of a larva of an arthropod species, the at least one wax having a melting temperature of at least 50° C.,
   wherein the baculovirus particle is completely enveloped by the coating.

2. The composite particle according to claim 1 further comprising an insecticide.

3. The composite particle according to claim 1, wherein the baculovirus particle is selected from an alphabaculovirus particle and a betabaculovirus particle.

4. The composite particle according to claim 1, wherein the baculovirus particle is in the form of a baculovirus occlusion body.

5. The composite particle according to claim 1, wherein the baculovirus particle is selected from *Heliothis zea* NPV, *Helicoverpa armigera* NPV, *Spodoptera exigua* NPV, *Spodoptera littoralis* NPV, *Spodoptera exempta* NPV, *Anticarsia gemmatalis* NPV, *Lymantria dispar* MNPV, *Neodiprion abietis* NPV, *Orygia pseudotsugata* NPV, *Neodiprion lecontei* NPV, *Trichoplusia ni* NPV, *Autographa californica* NPV, *Spodoptera albula* NPV, *Spodoptera litura* NPV, *Cydia pomonella* GV, *Plutella xylostella* GV, *Cryptophlebia leucotreta* GV, *Phthorimaea operculella* GV, *Adoxophyes orana* GV, *Homona maganima* GV, *Plodia interpunctella* GV, and *Adoxophyes honmai* GV.

6. The composite particle according to claim 1, wherein the wax is selected from waxes that are ingestible by a larva.

7. The composite particle according to claim 1, wherein the wax is a natural wax that is degradable and/or soluble in the gut of a larva.

8. The composite particle according to claim 1, wherein the wax is a mixture of waxes selected from mineral waxes and synthetic waxes and at least one natural wax wherein at least the natural wax is degradable and/or soluble in the gut of a larva.

9. The composite particle according to claim 1, wherein the natural wax is selected from carnauba wax, rice bran wax and candelilla wax and a mixture of two or more thereof.

10. The composite particle according to claim 1, wherein the arthropod species is a species from the order Lepidoptera and wherein the gut of the larvae of the arthropod species has a pH from 8 to 12.

11. A method of producing the composite particles according to claim 1 by
    i) melting a wax at a temperature of at least 50° C.;
    ii) adding the baculovirus particle to the molten wax of step i) and admixing therewith for a time period sufficient to at least partially coat said baculovirus particle;
    iii) rapidly cooling the product of step ii) to a solid; and
    iv) kibbling and comminuting the product of step iii) to a particle size for ingestion by a larva, wherein the wax is degradable and/or soluble in the gut of the larva of the arthropod species after completion of step iv.

12. The composite particle according to claim 1, wherein the composite particles has a volume mean diameter of less than 30 µm.

13. The composite particle according to claim 1, wherein the composite particles has a volume mean diameter in the range 8 µm to 15 µm.

14. A composition for application to crop plants that comprises the composite particles as defined in claim 1.

15. A composition for application to harvested and/or processed crop produce that comprises the composite particles as defined in claim 1 in dry form.

16. A crop plant coated with the composite particles as defined in claim 1.

17. A liquid formulation for controlling arthropod infestation of plants that comprises the composite particles according to claim 1 suspended within the liquid formulation.

18. A dry powder composition that is effective in controlling arthropod infestation in storage products that comprises the composite particles according to claim 1, wherein the dry powder composition is made up of:
    i) particles of wax that are degradable and/or soluble in the gut of larvae of at least one target arthropod species; and
    ii) at least partially encapsulated within the wax particles of i) at least one species of baculovirus in the form of baculovirus particles that has activity against the said arthropod larvae.

19. A method of controlling arthropod infestation, wherein the composite particles according to claim 1 are presented dry to the surfaces of grain or processed comestibles, or surfaces of storage areas by
    i) collecting the composite particles in a dusting apparatus;
    ii) releasing the said composite particles from the said dusting apparatus and onto the surfaces of said grain or processed comestibles.

20. A method of controlling arthropod infestation, wherein the composite particles according to claim 1 are admixed dry with grain or processed comestibles.

21. The composite particle according to claim 1, further comprising at least one UV blocker.

* * * * *